(12) United States Patent
Holsten et al.

(10) Patent No.: US 8,382,761 B2
(45) Date of Patent: Feb. 26, 2013

(54) SURGICAL STAPLE WITH ADJUSTABLE WIDTH BACKSPAN

(75) Inventors: Henry E. Holsten, Covington, GA (US); Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 586 days.

(21) Appl. No.: 12/186,250

(22) Filed: Aug. 5, 2008

(65) Prior Publication Data
US 2009/0062799 A1 Mar. 5, 2009

Related U.S. Application Data

(60) Provisional application No. 60/966,619, filed on Aug. 29, 2007.

(51) Int. Cl.
*A61B 17/56* (2006.01)
*A61B 17/58* (2006.01)
*A61B 17/064* (2006.01)
*A61B 17/84* (2006.01)
*A61F 2/30* (2006.01)

(52) U.S. Cl. ........................................ 606/75
(58) Field of Classification Search ............... 606/75
See application file for complete search history.

(56) References Cited

U.S. PATENT DOCUMENTS

| 3,807,394 | A | 4/1974 | Attenborough | |
|---|---|---|---|---|
| 3,862,631 | A | 1/1975 | Austin | |
| 3,900,025 | A * | 8/1975 | Barnes, Jr. | 606/71 |
| 4,428,376 | A | 1/1984 | Mericle | |
| 4,444,181 | A | 4/1984 | Wevers et al. | |
| 4,456,006 | A | 6/1984 | Wevers et al. | |
| 4,535,772 | A | 8/1985 | Sheehan | |
| 4,723,540 | A | 2/1988 | Gilmer, Jr. | |
| 4,852,558 | A | 8/1989 | Outerbridge | |
| 4,913,144 | A | 4/1990 | DelMedico | |
| 4,994,063 | A | 2/1991 | Garner | |
| 5,246,443 | A | 9/1993 | Mai | |
| 5,571,285 | A | 11/1996 | Chow et al. | |
| 5,634,926 | A | 6/1997 | Jobe | |
| 5,785,713 | A | 7/1998 | Jobe | |
| 6,051,007 | A | 4/2000 | Hogendijk | |
| 6,540,769 | B1 * | 4/2003 | Miller, III | 606/216 |
| 2002/0103489 | A1 | 8/2002 | Ku | |
| 2003/0139746 | A1 | 7/2003 | Groiso | |
| 2005/0251155 | A1 * | 11/2005 | Orban | 606/153 |

FOREIGN PATENT DOCUMENTS

| EP | 0301898 | 2/1989 |
|---|---|---|
| FR | 2801187 | 5/2001 |
| SU | 1114407 | 9/1984 |

* cited by examiner

*Primary Examiner* — Sameh Boles (57) ABSTRACT

A surgical staple comprising a first deformable leg member having at least a first portion of a staple backspan extending therefrom and a second deformable leg member having at least a second portion of the staple backspan extending therefrom. At least one of the first and second portions of the staple backspan are movable with respect to the other portion to vary the length of the staple backspan.

13 Claims, 5 Drawing Sheets

SURGICAL STAPLE WITH ADJUSTABLE WIDTH BACKSPAN

CROSS-REFERENCE TO RELATED APPLICATIONS

This application claims priority from provisional application Ser. No. 60/966,619, filed Aug. 29, 2007, the entire contents of which are incorporated herein by reference.

BACKGROUND

1. Technical Field

The present disclosure relates to surgical staples for use with surgical staplers and, more particularly, to surgical staples having an adjustable width backspan.

2. Description of Related Art

Surgical staples are highly specialized staples that can be employed during a variety of medical procedures (e.g., surgery). For example, closing skin wounds, anastomosing bowels, and excising portions of a lung are just a few of the many different types of medical procedures where surgical staples can be employed.

Clinicians and the likes have turned to surgical staplers and the surgical staples associated therewith as popular alternatives to traditional suturing methods in the medical environment. Incorporating a surgical stapler into a procedure allows a clinician to quickly and easily close tissue.

Current stapling technology can employ multiple same size surgical staples having first and second legs, and a backspan. As is the case with most conventional surgical staples, when the surgical staple is deployed, the surgical staple penetrates tissue, creating a hole(s) and an accompanying staple line. Located along the staple line and between the legs of the surgical staple is captured tissue. The captured and now transected tissue becomes hemostatic, which results in minimal leakage of bodily fluids around the transected tissue area. However, due to pressure changes in the body and/or other normal body processes (e.g., heating), tissue that is not captured between the legs of the surgical staple(s) may stretch and pull away from the surgical staple(s') legs, which may cause stress on the hole created by the surgical staple(s) and/or form a path in which bodily fluids may leak, both of which, in turn, can impede the healing process.

Therefore, a surgical staple that allows for relative motion between the legs of the surgical staple after the surgical staple has been deployed into tissue may be helpful.

SUMMARY

The present application provides a surgical staple comprising a first deformable leg member having at least a first portion of a staple backspan extending therefrom and a second deformable leg member having at least a second portion of the staple backspan extending therefrom. At least one of the first and second portions of the staple backspan is movable with respect to the other portion to vary the length of the staple backspan. In one embodiment, the legs members are movable in a direction substantially parallel to a longitudinal axis defined by the first portion of the staple backspan. The legs members preferably include a tissue piercing tip.

The present application also provides a surgical staple comprising a backspan defining a longitudinal axis, a first leg member disposed in mechanical cooperation with the backspan wherein at least a portion of the first leg member is translatable with respect to at least a portion of the backspan, and a second leg member disposed in mechanical cooperation with the backspan wherein at least a portion of the second leg member is translatable with respect to at least a portion of the backspan. In one embodiment, the legs members are movable in a direction substantially parallel to a longitudinal axis defined by the first portion of the staple backspan. The legs members preferably include a tissue piercing tip. In one embodiment, at least one of the legs members is configured for telescoping movement with respect to the backspan. In one embodiment, the backspan is coiled to form a spring with an opening to receive a portion of one of the leg members.

The present application also provides a staple cartridge for use with a surgical stapler comprising a plurality of surgical staples supported in a spaced relation to each other. Each of the surgical staples includes a first deformable leg member having at least a first portion of a staple backspan extending therefrom and a second deformable leg member having at least a second portion of the staple backspan extending therefrom. At least one of the first and second portions of the staple backspan is movable with respect to the other portion to vary the length of the staple backspan. In one embodiment, the legs members are movable in a direction substantially parallel to a longitudinal axis defined by the first portion of the staple backspan. The legs members preferably include a tissue piercing tip.

The present application also provides a surgical staple comprising a first leg member including a first portion, a second portion and a retaining structure, and a second leg member disposed in mechanical cooperation with the first leg member and including a first portion, a second portion and a retaining structure. The retaining structure of the first leg member is translatable with respect to the second portion of the second leg member and the retaining structure of the second leg member is translatable with respect to the second portion of the first leg member. In one embodiment, at least one of the retaining structures is a clasping member.

BRIEF DESCRIPTION OF THE DRAWINGS

Embodiments of the presently disclosed surgical staple with adjustable width backspan are disclosed herein with reference to the drawings, wherein.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions which follow, the term "proximal" will refer to the portion of a staple leg which is closer to a backspan of the staple, while the term "distal" will refer to the portion of a staple leg which is farther from the backspan.

Figure 1:
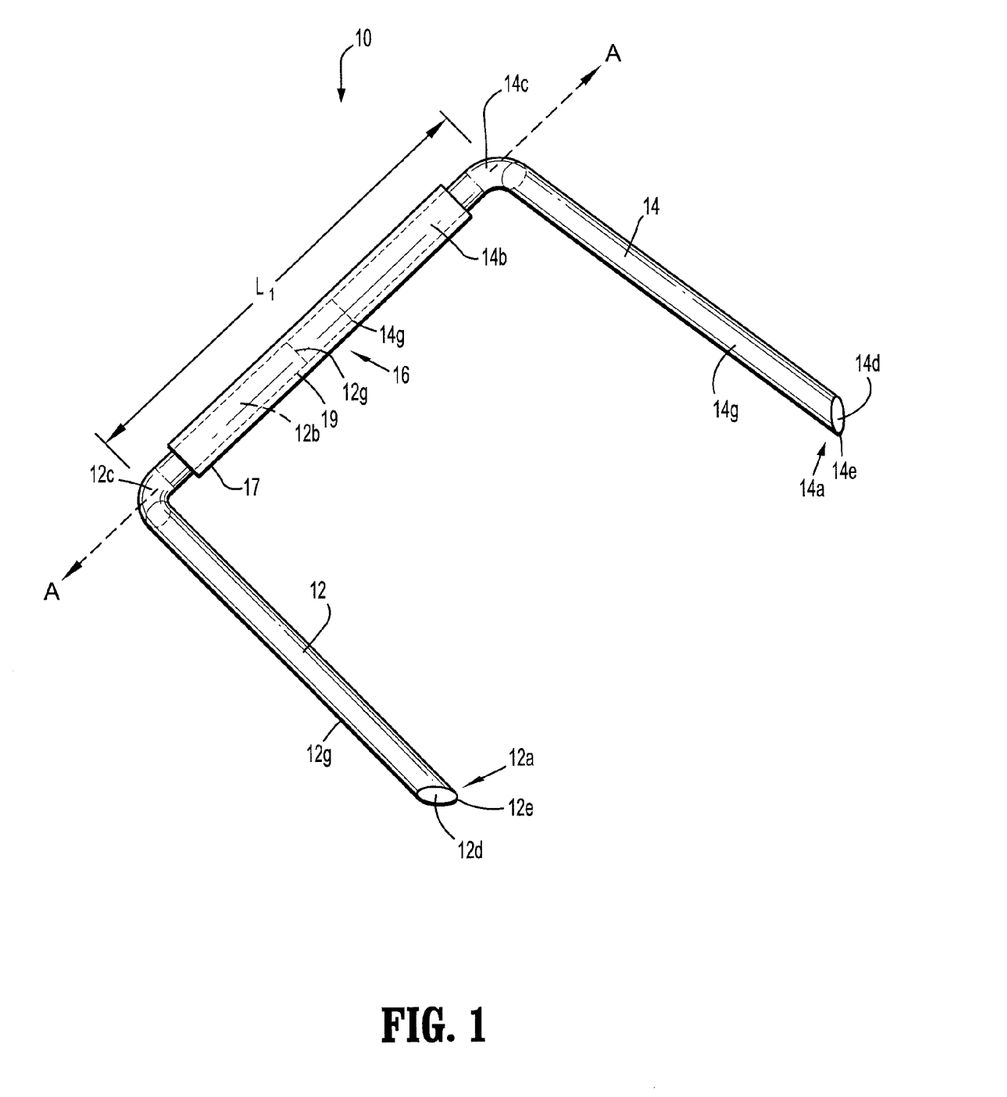
FIG. 1 is a perspective view of a surgical staple in accordance with a first embodiment of the present disclosure.
Figure 2A:
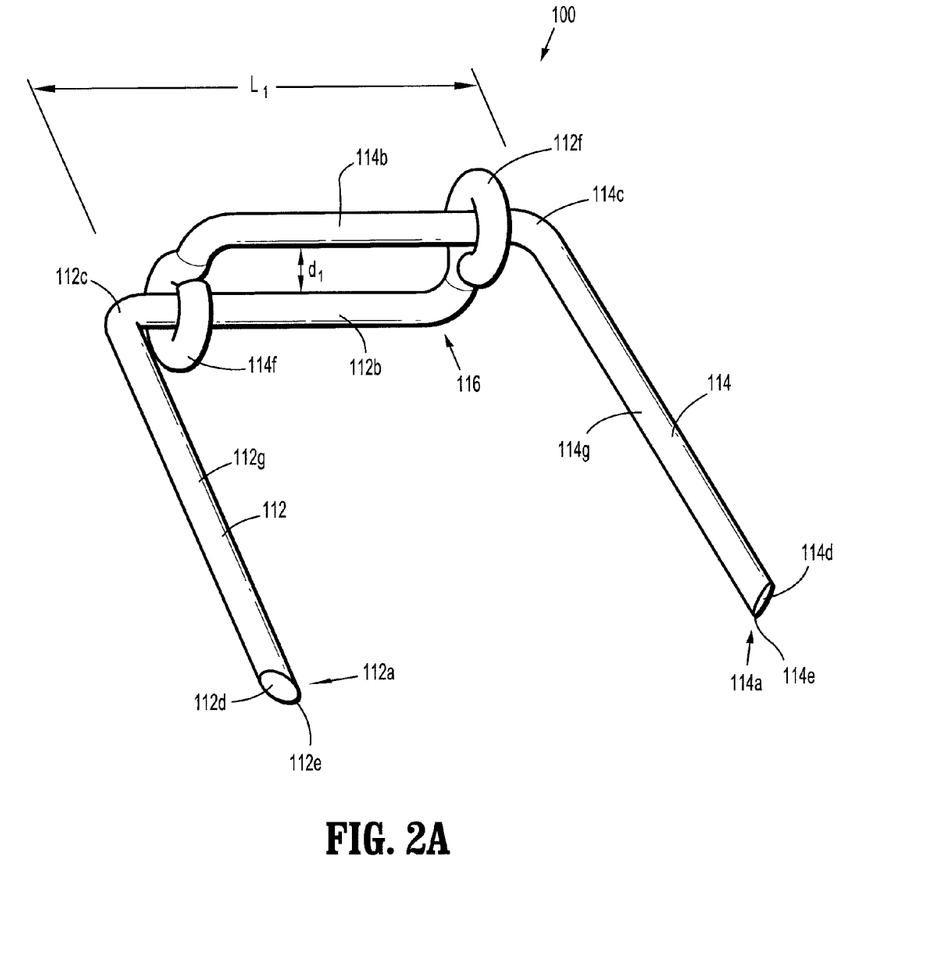
FIGS. 2A and 2B are perspective views of a surgical staple in accordance with alternate embodiments of the present disclosure.
Figure 2B:
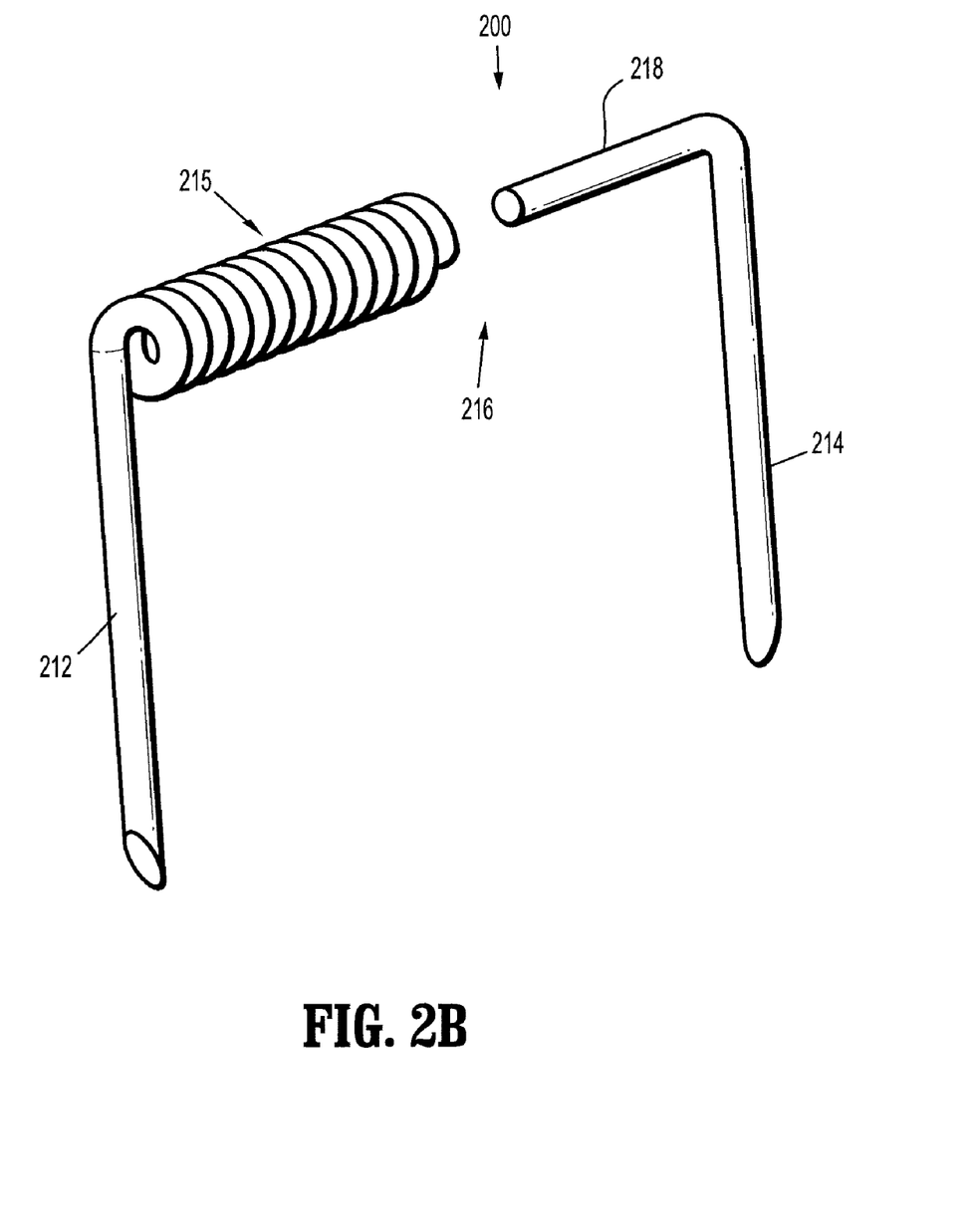

Surgical staples according to embodiments of the present disclosure are generally designated as reference number 10 in FIG. 1 and reference number 100 in FIG. 2. Surgical staple 10 (100) includes a first deformable leg member 12 (112) and a second deformable leg member 14 (114). First leg member 12 (112) includes at least a first backspan portion 12b (112b) extending transversely therefrom. Second leg member 14 (114) includes at least a second backspan portion 14b (114b) extending transversely therefrom. First and second portions 12b (112b), 14b (114b) of staple backspan 16 (116) are relatively movable as described in detail below to vary a length "$L_1$" of staple backspan 16 (116) prior to and/or subsequent to deformation of first and second leg members 12 (112) and 14 (114).

With specific reference to FIG. 1, surgical staple 10 includes backspan 16, first leg member 12 and second leg member 14. Backspan 16 as shown defines a longitudinal axis A-A and includes a tubular member 17 and a lumen or opening 19 formed therein to slidably receive backspan portions 12b and 14b. First leg member 12 is disposed in mechanical cooperation with backspan 16 and at least a portion of first leg member 12 is translatable with respect to at least a portion of backspan 16 (e.g. third backspan portion). Second leg member 14 is disposed in mechanical cooperation with backspan 16 and at least a portion of second leg member 14 is translatable with respect to at least a portion of backspan 16 (e.g. the third backspan portion). That is, as shown, backspan portions 12b, 14b of leg members 12, 14 are translatable with respect to each other within the lumen 19 of tubular member 17 of the backspan 16 to vary the overall length of the backspan as discussed below.

As shown in FIG. 1, first leg member 12 and second leg member 14 may be translatable in a direction substantially parallel to the longitudinal axis A-A. More specifically, at least one of first leg member 12 and second leg member 14 is configured for telescoping movement with respect to backspan 16, i.e. within the lumen 19 formed in the tubular member 17. In FIG. 1, both first leg member 12 and second leg member 14 are shown configured for such telescoping movement, as outer diameters of a portion of first leg member 12 and second leg member 14 (i.e. backspan portions 12b, 14b) are smaller than a corresponding inner diameter of lumen 19. Although described as tubular with a lumen, other variations are contemplated to provide a backspan with on opening or passage to receive the leg portions for sliding movement therein. For example, a single passage can be provided or a separate passage for each portion 12b, 14b. It is also contemplated that the backspan portions can slide over instead of within a backspan component or portion (e.g. over a tubular member) to adjust the distance between the staple legs 12, 14. Alternatively, the backspan portions can be configured for telescoping movement with respect to one another.

Backspan 16, first leg member 12, and/or second leg member 14, can include a retention or stop member for preventing first leg member 12 and/or second leg member 14 from dislodging from member 17 of backspan 16. The stop member (not explicitly shown) may be any suitable stop member including any combination of a lip, groove, angled portion, etc. It is envisioned that the stop member helps prevent first leg member 12 and/or second leg member 14 from extending past a predetermined location within member 17. Thus, first leg member 12 and/or second leg member 14 may have a maximum shift distance with respect to member 17, i.e. maximum distance backspan portions 12b, 14b can move. Movement of leg members 14 and 16 toward one another can also be limited if a continuous passage is provided as in lumen 17 as the ends 12g, 14g of portions 12b and 14b come into contact upon movement toward each other. Also movement can be limited as curves or intersections 12c, 14c contact the ends of member 17. A stop member can also be provided.

In other words, tubular member 17 is configured to substantially surround at least a portion of backspan portions 12b, 14b of the first leg member 12 and second leg member 14, wherein at least a portion of at least one of first leg member 12 and second leg member 14 is translatable at least partially within tubular member 17 and tubular member 17 is preferably substantially hollow. In the illustrated embodiment, both first leg member 12 and second leg member 14 are translatable at least partially within backspan 16, and more particularly, backspan portions 12b, 14b move within aperture or lumen 19 of tubular member 17.

In the embodiment shown in FIG. 1, first leg member 12 includes a tissue piercing distal tip 12a and first backspan portion 12b (shown partially in phantom in FIG. 1), and an intersection or transition portion 12c joining the first portion 12b with deformable leg portion 12g. Similarly, second leg member 14 includes a tissue piercing distal tip 14a and a second backspan portion 14b (shown partially in phantom in FIG. 1), and an intersection or transition portion 14c joining the first portion 14b with deformable leg portion 12g. While intersections 12c and 14c are shown as arcuate intersections, other types of intersections, corners or junctions, such as angled intersections may be employed. Additionally, each of first leg member 12 and second leg member 14 in the unformed condition is substantially "L" shaped in the embodiment depicted in FIG. 1 although other shapes are contemplated.

In an alternative embodiment, backspan 16 may have one of either first leg member 12 or second leg member 14 integrally formed therewith or non-movably attached thereto and the opposing leg member configured for translation therewith. For example, where first leg member 12 and backspan 16 are not translatable with respect to one another, only second leg member 14 would be able to shift relative to backspan 16. Similarly, where second leg member 14 and backspan 16 are not translatable with respect to one another, only first leg member 12 would be able to shift relative to backspan 16.

First leg member 12, second leg member 14 and backspan 16 can be made from the same material as one another or can be made of different materials. Any suitable material may be used to make these components of surgical staple 10 including but not limited to stainless steel, titanium, a biocompatible material, plastic, and the like. In one embodiment, at least a portion of surgical staple 10 is made from titanium. Having a surgical staple 10 made from titanium has certain advantages over a surgical staple made from stainless steel. For example, an MRI procedure can be performed on a patient having a titanium surgical staple 10 without concerns of the surgical staple interfering with the MRI procedure, as titanium is non-magnetic. Conversely, a surgical staple made from stainless steel may interfere with an MRI procedure, which, in turn, can lead to delays and/or additional operating costs to the medical facility.

As mentioned above, first leg member 12 and second leg member 14 in the preformed position can be oriented in a relatively fixed position in a substantially parallel spaced relation to each other. It is also envisioned that first leg member 12 and second leg member 14 may be oriented in a different relation to each other. For example, first leg member 12 and/or second leg member 14 can be oriented such that they form an acute and/or obtuse angle with respect to backspan 16 prior to formation, thus not necessarily being parallel to one another.

In one embodiment, the elements of each leg member 12, 14 (e.g., tissue piercing distal tip 12a, first portion 12b, and intersection 12c) can be integrally formed as one piece. However, it is contemplated that one or more of tissue piercing distal tip 12a, first portion 12b, and intersection 12c can be individual members joined together by any suitable means.

As disclosed herein, the tissue piercing distal tip (e.g., 12a of first leg member 12) can have a generally slanted profile 12d forming a pointed tip 12c. The inclusion of generally slanted profile 12d forming a pointed tip 12e may facilitate piercing of tissue. A centrally located sharpened tip is also contemplated. In an alternate embodiment, the tissue piercing distal tip (e.g. 12a) can have a relatively straight profile without a pointed tip (e.g., a substantial blunt tip).

Figure 1A:
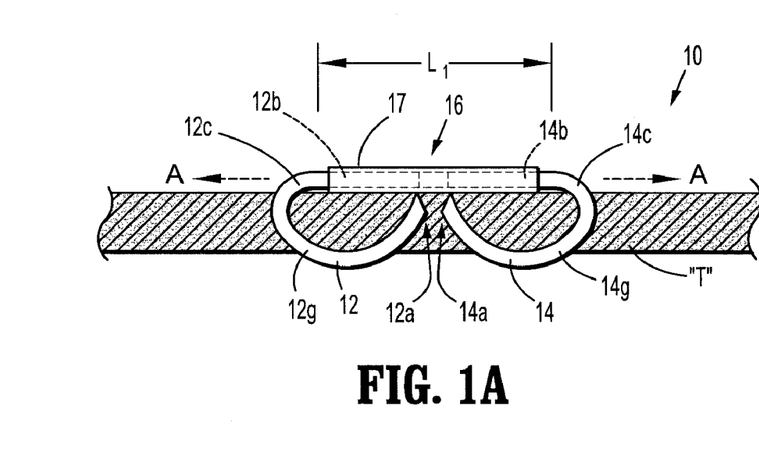
FIG. 1A is a side view of the surgical staple of FIG. 1, illustrating leg members in a deformed orientation and through a layer of tissue
Figure 1B:
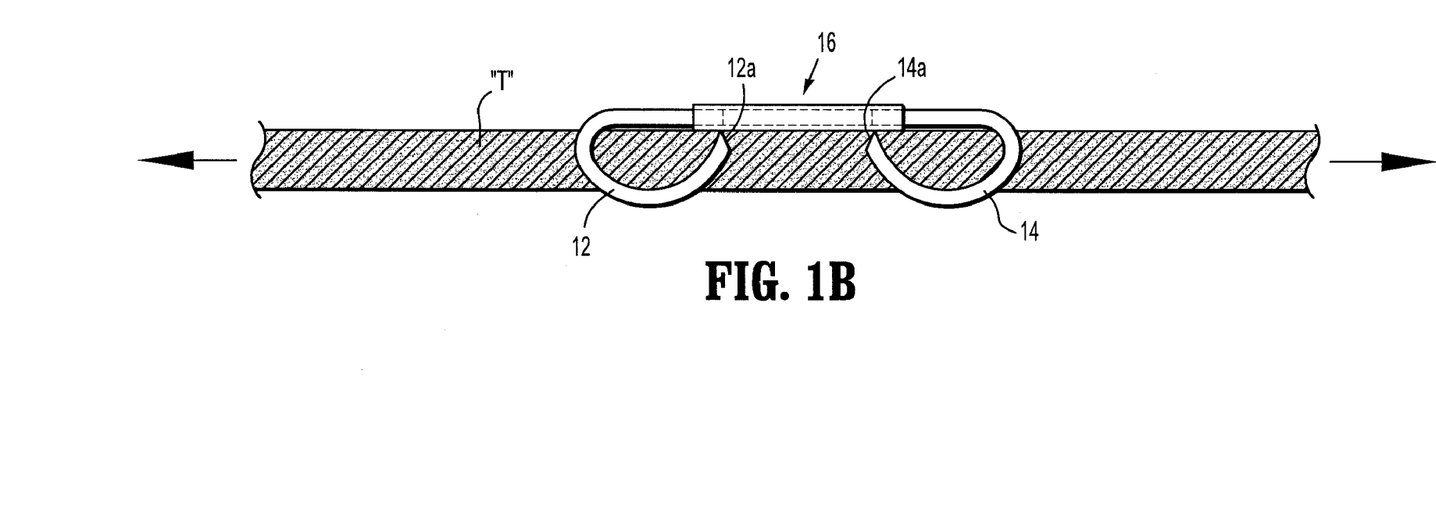
FIG. 1B is a side view similar to FIG. 1A illustrating the tissue stretched and the staple legs moved outwardly with respect to the backspan.

FIG. 1A illustrates surgical staple 10 of FIG. 1 in a deformed orientation and through a layer of tissue "T." Specifically, first leg member 12 and second leg member 14 are shown in a deformed condition having a substantially curved shape. It is envisioned that the length "$L_1$" of the overall backspan can be varied by movement of staple legs 12, 14, prior to the staple being ejected from a staple cartridge 200 (discussed below) which changes the length of exposure of the backspan portions 12b, 14b. Staple leg members 12 and 14 then pierce tissue "T" and contact an anvil. Anvil causes staple leg members 12 and 14 to deform into a substantial B-like shape as shown in FIG. 1A. Alternatively, instead of or in addition to changing the backspan length prior to ejection, the length of the overall backspan can be varied after the staple is formed in tissue by movement of the staple legs 12, 14. This change in overall backspan length is a result of the length of the backspan portions 12b, 14b extending from component 17. FIG. 1B illustrates by way of example movement of the staple leg members 12, 14 outwardly with respect to the backspan as a result of the stretching of tissue T.

With specific reference to the alternate embodiment of FIG. 2A surgical staple 100 includes first leg member 112 and second leg member 114. First leg member 112 includes a distal tip 112a, a first backspan portion 112b, a retaining structure 112f (or clasping member) and deformable leg portion 112g. Second leg member 114 is disposed in mechanical cooperation with first leg member 112 and includes a distal tip 114a, a first backspan portion 114b, a retaining structure 114f (or clasping member) and deformable leg portion 114g. In the illustrated embodiment, retaining structure 112f of first leg member 112 is translatable with respect to first backspan portion 114b of second leg member 114, and retaining structure 114f of second leg member 114 is translatable with respect to first backspan portion 112b of first leg member 112. As can be appreciated, translation of at least one leg member (e.g., first leg member 112) with respect to the other leg member (e.g., second leg member 114) alters length "$L_1$" of backspan 116. Further, translation of first leg member 112 is bound in one direction by an intersection 114c or transition portion of second leg member 114 and is bound in the opposite direction by retaining structure 114f of second leg member 114. Similarly, translation of second leg member 114 is bound in one direction by an intersection or transition portion 112c of first leg member 112 and is bound in the opposite direction by retaining structure 112f of first leg member 112.

It is contemplated that surgical staple 100 can also include previously described operative features, and/or parts associated with first and second leg members 12 and 14 of surgical staple 10. That is, for example, each of first and second leg members 112 and 114 can include a tissue piercing distal end 112a, 114a, respectively, or a substantially blunt tip. In accordance with the embodiment shown in FIG. 2A, backspan portion 112b of first leg member 112 and backspan portion 114b of second leg member 114 may be substantially parallel with one another, defining a distance "$d_1$" therebetween.

With continued reference to FIG. 2A, clasping member 112f is formed at an end of first backspan portion 112b of first leg member 112 and is configured to engage a portion of backspan portion 114b of second leg member 114 forming a slidable connection therebetween. Clasping member 114f is formed at an end of backspan portion 114b of first leg member 114 and is configured to engage a portion of backspan portion 111b of first leg member 112 forming a slidable connection therebetween. In the illustrated embodiment, clasping members 112f, 114f include a generally hook-like shape. It will be appreciated by those skilled in the relevant art that the shape of clasping members 112f, 114f can be any suitable shape known the available art that will allow clasping member 112f to engage a portion of second leg member 114 and provide a slidable connection therebetween.

In an alternate embodiment of FIG. 2B, staple legs 212 and 214 of staple 200 are joined by a coiled backspan 215 of staple backspan 216. Coiled backspan 215 extends from leg 212. More specifically, backspan 215 is coiled into a spring and preferably integral with the staple leg 212. The backspan portion 218 of staple leg 214 is received within, and moves within, the opening in the coil to adjust the distance of the legs 212, 214 with respect to one another to achieve the function described herein with respect to the other embodiments, i.e. to vary the overall length of backspan 216.

As can be appreciated, surgical staples 10 (100, 200), as described herein, enable length "$L_1$" of backspan 16 (116, 216) to be varied prior to deformation of first and second leg members 12 (112, 212), 14 (114, 214). For instance, the length "$L_1$" of the backspan is able to be varied to fit within a desired staple cartridge.

Additionally, surgical staples 10 (100, 200), as described herein, enable relative movement between a portion of the surgical staple and the tissue that the surgical staple has been deployed in. In typical operation, a clinician will deploy staple(s) 10 (100, 200) into tissue of a patient to close a wound associated therewith. For the reasons previously disclosed, tissue adjacent the staple(s) 10 (100, 200) may begin to pull away from first and second leg members 12 (112, 212) and 14 (114, 214), respectively. As tissue begins to pull away from first and second leg members 12 (112, 212) and 14 (114, 214), either or both of first and second leg members 12 (112, 212), 14 (114, 214) will shift relative to the opposite leg member (changing the length of the backspan) which, in turn, will reduce and/or prevent tissue separation (see e.g. FIG. 1B).

Figure 3:
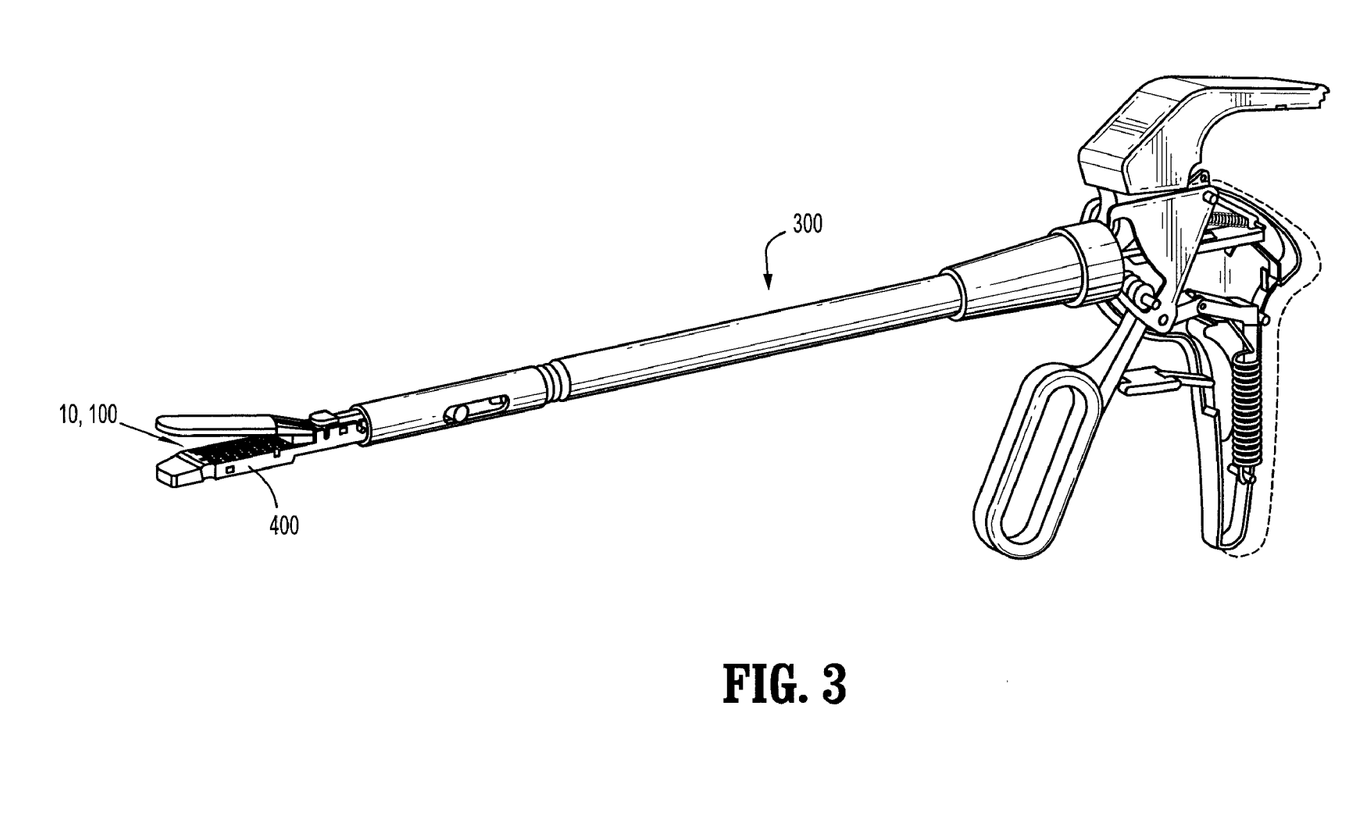
FIG. 3 is a perspective view of one type of surgical stapler for applying the surgical staples of the present disclosure

With reference to FIG. 3, the present disclosure also relates to a staple cartridge 400 for use with a surgical stapler 300. Staple cartridge 400 includes a plurality of surgical staples 10, 100, or 200 as described above, supported in a spaced relation to each other. It is envisioned that staple cartridge 400 may be a replaceable staple cartridge 400. Further, staple cartridge 400 may house a plurality of surgical staples 10, 100, 200 arranged in at least two lateral rows and may be mountable in a cartridge channel of a cartridge assembly. While a particular type of surgical stapler 300 is illustrated in FIG. 3, the staple cartridge of the present disclosure may be used in connection with any suitable surgical stapler, including for example, open staplers and endoscopic staplers applying one or more linear rows of staples sequentially or simultaneously and staplers applying a circular array of staples.

It will be understood that various modifications may be made to the embodiments disclosed herein. For example, it is envisioned that surgical staple 10 of the present disclosure may be configured such that the backspan includes a bellows member to allow for further and/or more controlled translation of at least one leg member with respect to the backspan. Also, although the leg members are shown in each of the embodiments as being substantially parallel to each other, and substantially perpendicular to the backspan in the preformed position, alternatively one or both of the legs could form an acute or obtuse angle with respect to the backspan in the preformed position. Therefore, the above description should not be construed as limiting, but merely as exemplifications of various embodiments. Those skilled in the art will envision other modifications within the scope and spirit of the claims appended hereto.

What is claimed is:

1. A surgical staple, comprising:
   a first deformable leg member having at least a first portion of a staple backspan extending therefrom, the first leg member deformable from an initial insertion condition extending transversely from the backspan to a deformed condition, a penetrating tip of the first leg member being further from the backspan in the initial condition; and
   a second deformable leg member having at least a second portion of the staple backspan extending therefrom, the second leg member deformable from an initial insertion condition extending transversely from the backspan to a deformed condition, a penetrating tip of the second leg member being further from the backspan in the initial condition;
   wherein the first portion of the staple backspan includes a first retaining structure having a first opening configured to receive the second portion of the staple backspan therethrough and the second portion of the staple backspan includes a second retaining structure having a second opening configured to receive the first portion of the staple backspan therethrough such that at least one of the first and second portions of the staple backspan are movable with respect to the other portion to vary a length of the staple backspan,
   wherein the first and second retaining structures are interconnected to each other such that subsequent to the first and second portions of the staple backspan being received within the second and first openings of the second and the first retaining structures, the first and second deformable leg members are movable away from one another in response to movement of tissue, wherein translation of the first and second deformable leg members away from one another is restricted as a result of contact between the first and second retaining structures.

2. The surgical staple according to claim 1, wherein at least one of the first leg member and the second leg member is movable in a direction substantially parallel to a longitudinal axis defined by the first portion of the staple backspan.

3. The surgical staple according to claim 1, wherein the first leg member and the second leg member are substantially L-shaped.

4. The surgical staple according to claim 1, wherein the first leg member and the second leg member each include a tissue-piercing tip.

5. The surgical staple according to claim 1, wherein at least one of the first and second portions of the staple backspan are movable prior to deformation of the first and second leg members.

6. A surgical staple, comprising:
   a backspan having first and second backspan portions and defining a longitudinal axis, the first backspan portion includes a first retaining structure having a first opening configured to receive the second portion therethrough and the second backspan portion includes a second retaining structure having a second opening configured to receive the first backspan therethrough;
   a first leg member disposed in mechanical cooperation with the backspan portion, at least a portion of the first leg member being translatable with respect to the second backspan portion, the first leg member deformable from an initial insertion condition extending transversely from the backspan to a deformed condition, a penetrating tip of the first leg member being further from the backspan in the initial condition; and
   a second leg member disposed in mechanical cooperation with the second backspan portion, at least a portion of the second leg member being translatable with respect to the first backspan portion, the second leg member deformable from an initial insertion condition extending transversely from the backspan to a deformed condition, a penetrating tip of the second leg member being further from the backspan in the initial condition,
   wherein the first and second retaining structures are interconnected to each other such that subsequent to the first and second portions of the staple backspan being received within the second and first openings of the second and the first retaining structures, the first and second deformable leg members are movable away from one another in response to movement of tissue, wherein translation of the first and second deformable leg members away from one another is restricted as a result of contact between the first and second retaining structures.

7. The surgical staple according to claim 6, wherein the first leg member and the second leg member are translatable in a direction substantially parallel to the longitudinal axis.

8. The surgical staple according to claim 6, wherein the first leg member and the second leg member are substantially L-shaped.

9. A surgical staple, comprising:
   a deformable first leg member including a first portion, a second portion and a retaining structure, the first leg member deformable from an initial insertion condition extending transversely from the backspan to a deformed condition, a penetrating tip of the first leg member being further from the backspan in the initial condition; and
   a deformable second leg member disposed in mechanical cooperation with the first leg member, the second leg member including a first portion, a second portion and a retaining structure, the second leg deformable from an initial insertion condition extending transversely from the backspan to a deformed condition, a penetrating tip of the second leg being further from the backspan in the initial condition,
   wherein the retaining structure of the first leg member is translatable with respect to the second portion of the second leg member, and wherein the retaining structure of the second leg member is translatable with respect to the second portion of the first leg member,
   wherein the first and second retaining structures are interconnected to each other such that subsequent to the first and second portions of the staple backspan being received within the second and first openings of the second and the first retaining structures, the first and second deformable leg members are movable away from one another in response to movement of tissue, wherein translation of the first and second deformable leg members away from one another is restricted as a result of contact between the first and second retaining structures.

10. The surgical staple according to claim 9, wherein the second portion of the first leg member and the second portion of the second leg member are substantially parallel with one another.

11. The surgical staple according to claim 9, wherein at least one of the retaining structure of the first leg member and the retaining structure of the second leg member is a clasping member.

12. The surgical staple according to claim 9, wherein translation of at least one leg member with respect to the other leg member alters a distance between the second portions of the leg members.

13. The surgical staple according to claim 9, wherein translation of the first leg member is bound in one direction by the second portion of the second leg member and is bound in the opposite direction by the retaining structure of the second leg member.

* * * * *